United States Patent [19]

Peterson et al.

[11] Patent Number: 5,098,405
[45] Date of Patent: Mar. 24, 1992

[54] APPARATUS AND METHOD FOR A SIDE PORT CATHETHER ADAPTER WITH A ONE PIECE INTEGRAL COMBINATION VALVE

[75] Inventors: Gerald H. Peterson; Wallace H. Ring, both of Salt Lake City, Utah

[73] Assignee: Becton, Dickinson and Company, Franklin Lakes, N.J.

[21] Appl. No.: 648,799

[22] Filed: Jan. 31, 1991

[51] Int. Cl.⁵ .............................................. A61M 5/00
[52] U.S. Cl. .................................. 604/247; 604/246; 604/256
[58] Field of Search ............... 604/246, 247, 256, 283, 604/905, 169, 167, 164, 9, 30, 264; 137/606, 846

[56] References Cited

U.S. PATENT DOCUMENTS

| | | |
|---|---|---|
| 3,385,301 | 5/1968 | Harautuneian . |
| 3,416,567 | 12/1968 | von Dardel et al. ............ 604/83 X |
| 3,572,375 | 3/1971 | Rosenberg . |
| 3,710,942 | 6/1973 | Rosenberg . |
| 4,063,555 | 12/1977 | Ulinder . |
| 4,084,606 | 4/1978 | Mittleman ..................... 604/237 X |
| 4,106,491 | 8/1978 | Guerra ............................. 604/169 X |
| 4,871,356 | 10/1989 | Haindl et al. ..................... 604/247 |

Primary Examiner—John J. Wilson
Assistant Examiner—Jeffrey A. Smith
Attorney, Agent, or Firm—Arthur D. Dawson

[57] ABSTRACT

A catheter adapter, with a side port connection, contains a one-piece integral bifunctional resilient combination valve which serves to prevent back flow from the patient. It allows infusion from either the primary axial port or from the side port and provides automatic shut-off when the infusion pressure becomes lower than the ambient pressure in the patient's body from either port.

18 Claims, 4 Drawing Sheets

APPARATUS AND METHOD FOR A SIDE PORT CATHETHER ADAPTER WITH A ONE PIECE INTEGRAL COMBINATION VALVE

FIELD OF THE INVENTION

This invention relates to side port adapters and more particularly, valves within such adapters to prevent back flow.

BACKGROUND

Side port adapters may be added to an inserted catheter to provide an additional site for infusion; in particular, a side port adapter could be attached to the adapter of a placed catheter. Specifically, over the needle catheters, used for peripheral intravenous entry into the vasculature of a patient, provide an easily attached access port to connect to for infusion and/or sampling. The addition of a side port adapter to the adapter of the catheter would permit connection of more than one line or a line and a syringe to the placed catheter.

Side port adapters with internal valving have been patented and used to control flow through the passageways of the adapter. Valves of various designs located in side port adapters have been useful for different purposes. For example, U.S. Pat. No. 3,385,301 shows a balloon catheter with a deformable one way inflation valve wherein a resilient valve member is captured in one leg of a Y-adapter through which a syringe may be used to collapse the valve thus opening that path to air for inflating the balloon.

A side port catheter adapter with a valve, shown in U.S. Pat. No. 3,416,567, has a capped side port and a flexible tube within a main passage of that adapter. An arrangement such as shown in the '567 patent selectively permits introduction of medication through the side port but prevents back flow through the side port after the introduction. A syringe can be used to inject fluid and collapse sufficiently the sleeve in the main passage thus opening the valve with the pressure of the flowing injectate as it moves from the syringe. Various other valves have been tried for a similar purpose as in U.S. Pat. No. 4,063,555.

In U.S. Pat. No. 3,572,375, a twin valve T-connector is disclosed for use with syringes and injection devices. There is a coupling body having three interconnected passageways with separate independent check valves in two of the passageways. Each check valve may be independently and separately used for controlling to a single direction the flow of fluid through a respective passage of the coupling body. Duck bill check valves are shown, while the arrangement is similar to the concept presented herein, that couplinq body with valves is not identical since the side port intersects with the main passage proximal relative to the check valve. Consequently, two independent separate check valves are required instead of one as is disclosed and claimed herein.

U.S. Pat. No. 3,710,942 shows a twin passage, double valve arrangement wherein foam is used to encourage closure of the check valve and prevent backflow. In addition to the duck bill shaped check valves, mushroom style valves of various shapes are disclosed. The valves are separate and independent from one another and the intersection of the passages are not positioned as disclosed herein.

Problems with the various known valves including luer activated valves include not providing reliable activation of an automatic valve within the adapter and valves that require they be opened by contact with another device which may pass infection. The side port adapter with a combination valve as shown and disclosed herein overcomes the problems of the aforesaid valves and side port adapters. In addition, the removable side port adapter provides flexibility in that the side port can be removed after the appropriate period of use, thus preventing subsequent potential contamination or misuse.

An alternative to the use of a side port adapter with valve as described herein would be the use of a standard three-way stopcock as an add on infusion site. This, however, requires that the stopcock lever be manually actuated to open the desired flow paths. This can be confusing, is not automatic, and does not provide the anti backflow valve in the main channel.

SUMMARY OF THE INVENTION

A combination valve for a side port adapter to prevent back flow through the side port and through a main channel has an adapter having its main channel along an axis thereof. The side port most preferably intersects with the main channel to provide access for flow therethrough. A resilient member with a passage therethrough has disposed therein a check valve located substantially normal to the axis and across the passage. The check valve opens with flow along the axis in a direction and closes to flow in an opposite direction. The resilient member is normally against the intersection to close the intersection until the member deflects and opens under fluid pressure within the side port exceeding its resilience.

The main channel may have an inlet and an outlet associated therewith and positioned along the axis. The outlet in the preferred embodiment is a male luer for easy fluid tight connection to a catheter. The inlet in the preferred embodiment is a female luer for easy fluid tight connection with a mating fluid supply having a luer connection and arranged to provide flow through the main channel to the outlet. The check valve within the resilient member functions to prevent fluids injected through the side port from flowing toward the main channel inlet, forcing the fluid to flow toward the main channel outlet, and thus insuring the most rapid introduction into a patient's vascular system. The check valve may include a web across the passage with a normally closed slit. The web is shaped to open when subject to flow in the direction from inlet to the outlet and to resist opening when subject to flow in the opposite direction.

The web shape most preferable is that of a duck bill that opens when subject to pressure that would force flow in the direction through the duck bill and resists opening when subject to pressure that would tend to force flow in the opposite direction into the duck bill. The resilient member is preferably a cylindrical shape and the main channel is also a cylindrical shape to receive the resilient member. The cylindrical shape may preferably have a circular cross section. The substantially cylindrical resilient member most preferably has an edge at a distal end thereof. The adapter has an annular shoulder disposed within the main channel distal along the axis and relative to the side port to locate the edge of the cylindrical member within the main channel.

A method of providing a combination valve in a side port adapter to prevent back flow therethrough may include the step of providing an adapter with a main channel and a side port that intersects with the main channel. That step is followed by the step of placing a resilient member having a passage therethrough in the main channel to cover the intersection and prevent flow from the outlet to the side port. The step of providing a duck bill check valve in the passage permits flow through the main channel in the direction from inlet to outlet and prevents flow in the opposite direction. Added steps may include packing and sterilizing the valve and adapter.

DETAILED DESCRIPTION OF THE DRAWINGS

Figure 1:
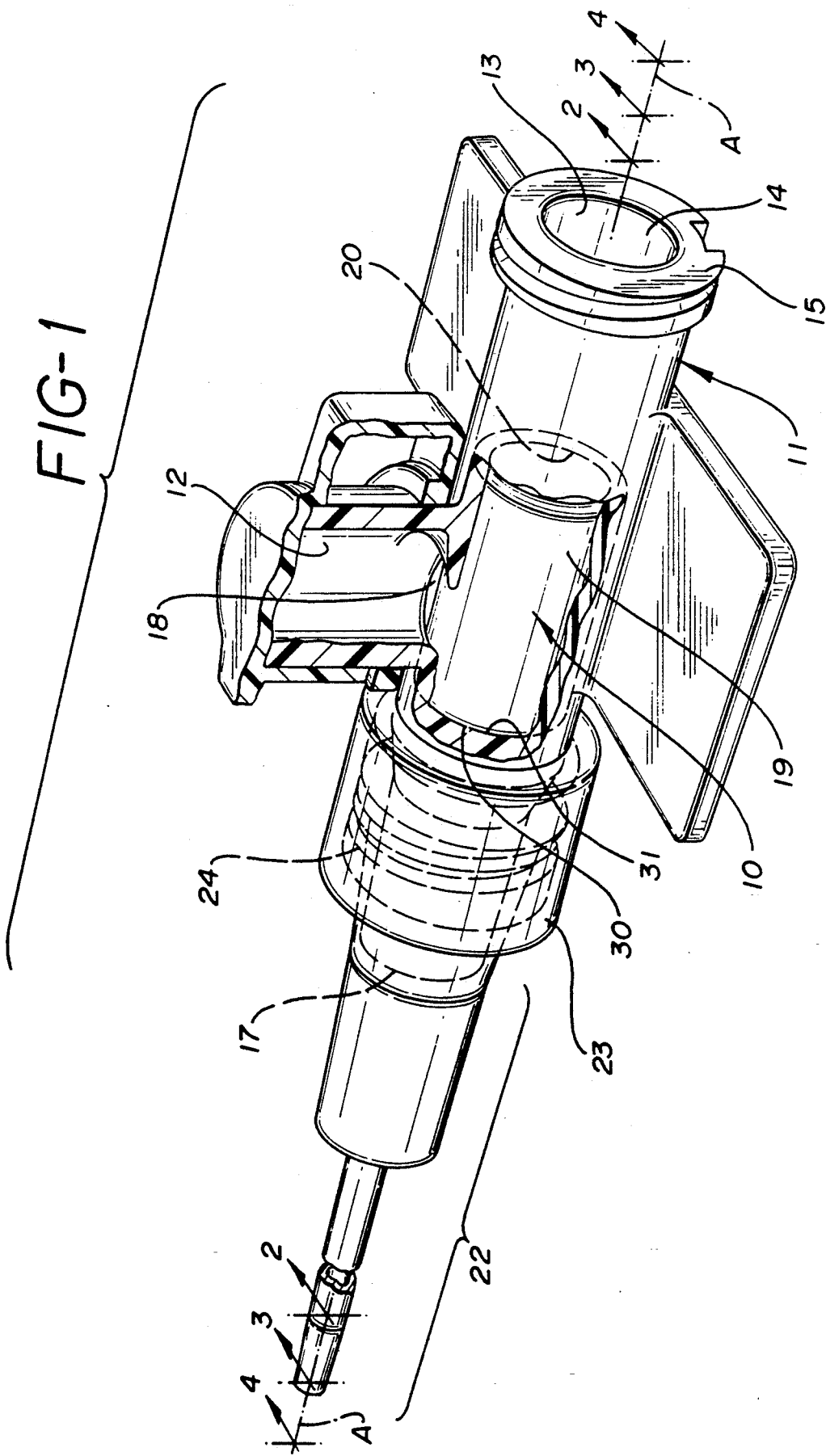
FIG. 1 is a perspective view of the preferred embodiment of a combination valve shown in a side port adapter which is partially in cross section so the location of the combination valve in its side port adapter is apparent.

While this invention is satisfied by embodiments in many different forms, there is shown in the drawings and will herein be described in detail, a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

FIG. 1 shows a perspective view of a combination valve 10 for a side port adapter 11 with the adapter 11 partially in cross section in order to show the location of the combination valve 10. The adapter 11 includes a side port 12 and a main channel 13. An axis "A" is centered in the main channel 13 and the main channel 13 has an inlet 14 at its proximal end 15 and an outlet 16 at its distal end 17. Proximal is used herein relative to the position of the medic and distal relative to the patient and as the adapter 11 would normally be used. There is an intersection 18 formed where the side port 12 meets the main channel 13. The intersection 18 provides access for flow between the side port 12 and the main channel 13.

Figure 2:
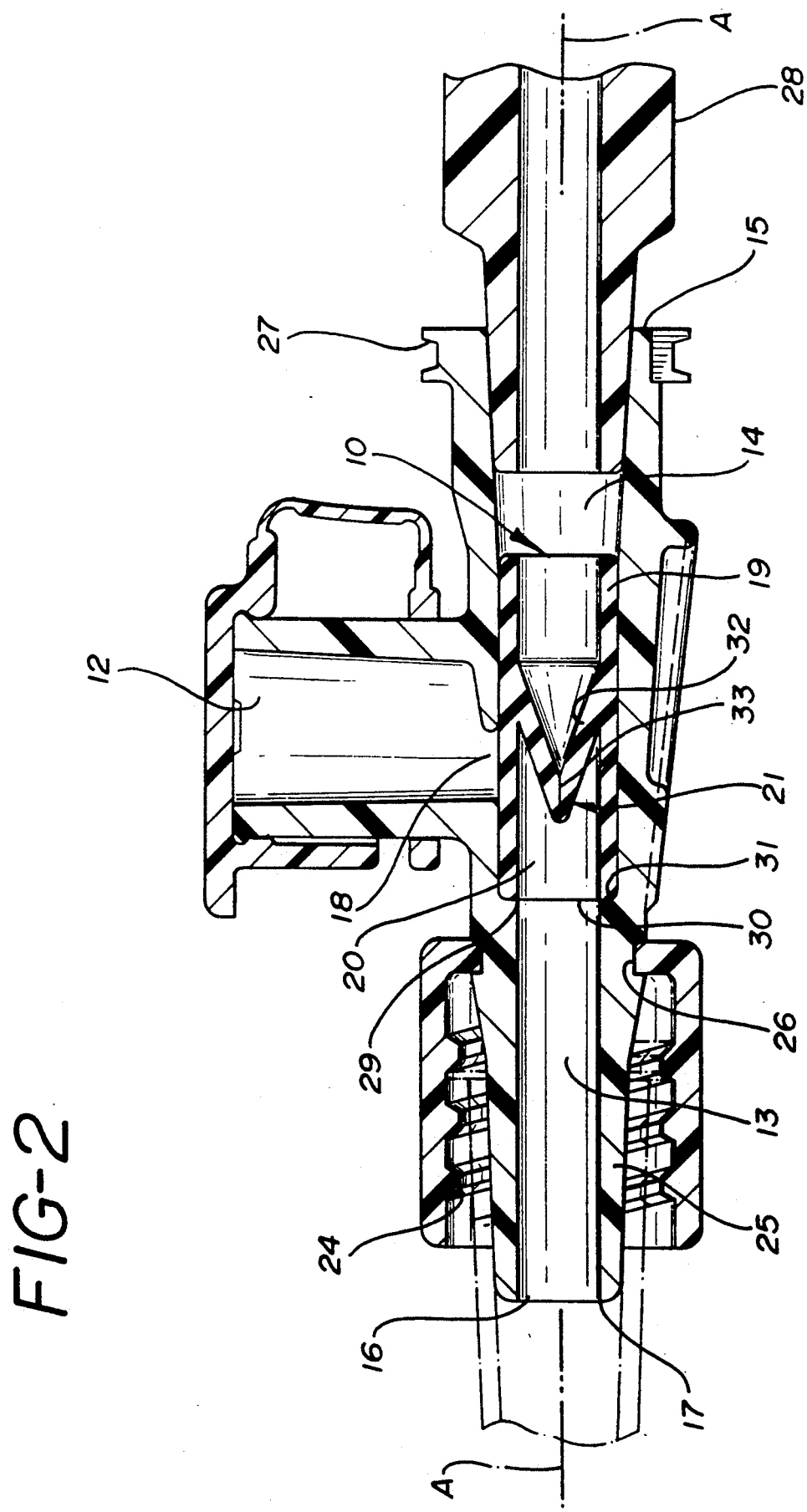
FIG. 2 is a side cross-section view, taken along lines 2—2 in FIG. 1 and showing the side port adapter and the combination valve in cross-section.
Figure 3:
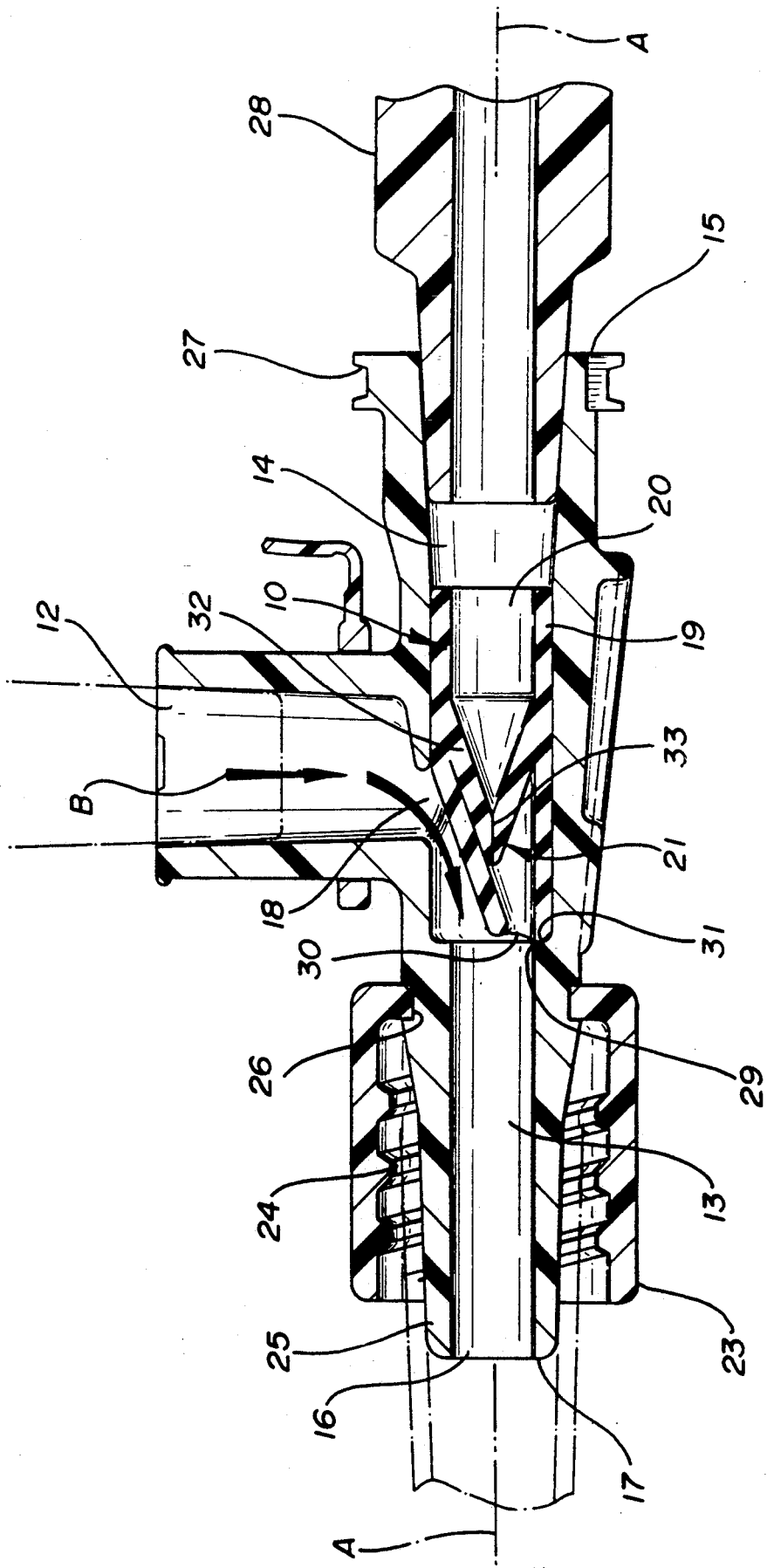
FIG. 3 is a side cross-sectional view similar to FIG. 2, taken along lines 3—3 in FIG. 1 and illustrating how the combination valve deflects under flow through the side port.
Figure 4:
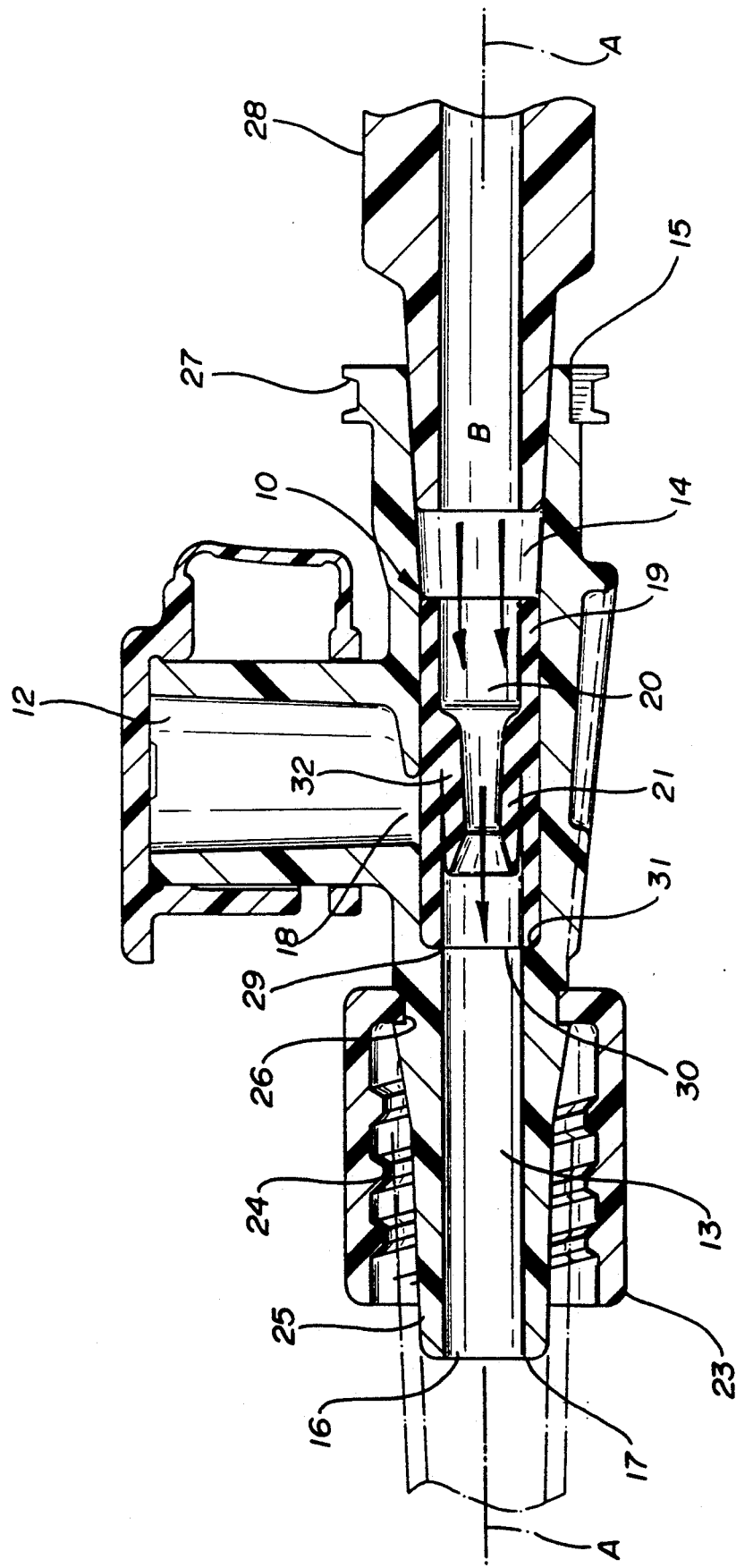
FIG. 4 is a side cross sectional view similar to FIG. 2, taken along lines 4—4 in FIG. 1 and illustrating how the combination valve opens due to flow through the main channel.

As shown in FIGS. 1 through 4, the combination valve 10 includes a substantially cylindrical resilient member 19 having a passage 20 therethrough. The passage 20 is aligned with the main channel 13 and centered about the axis "A". Positioned substantially normal to the axis "A" and across the passage 20 is a check valve 21 which opens when subjected to flow in a direction designated "B" as illustrated in FIG. 4 and shown by arrows. The flow is from the inlet 14 to the outlet 16. The check valve 21 is substantially closed to flow in an opposite direction, i.e. from the outlet 16 to the inlet 14,
see FIG. 2. The substantially cylindrical resilient member 19 is dimensioned such that it fits snugly within the main channel 13 of the adapter 11. The substantially cylindrical resilient member 19 thus closes the side port 12 of the intersection 18 with the main channel 13 as shown in FIGS. 1, 2 and 4. By maintaining its cylindrical shape until the intersection 18 is opened under fluid pressure from the side port, member 19 acts to prevent back flow from the outlet 16 to the side port 12. Similarly, flow from the inlet 14 to the side port 12 is prevented. When this side port fluid pressure exceeds the resilience of the substantially cylindrical resilient member 19 and causes deflection of the member 19 as shown in FIG. 3, flow through the side port 12 begins. Pressure sufficient to exceed the resilient or restoring force of the substantially cylindrical member 19 is required.

While not essential, it is useful to have a catheter 22, as in FIG. 1, connected in fluid tight communication with the outlet 16. For this purpose, there is a rotatable luer collar 23 having internal female threads 24. The rotatable luer collar 23 rotates about a male luer taper 25 over the outlet 16 of the adapter 11 by in an annular groove 26 positioned proximally about the male luer taper 25. The adapter 11 is provided with a luer thread 27 around the inlet 14 such that a fluid supply 28 may be connected via a mating luer connector to the inlet 14 to provide flow through the main channel 13, as shown in FIGS. 2, 3 and 4.

The substantially cylindrical resilient member 19 has an edge 29 at a distal end 30 thereof. The edge 29 is first inserted into the adapter 11 during assembly of the substantially cylindrical member 19 into the adapter 11. There is an annular shoulder 31 disposed within the main channel 13 and positioned distal along the axis "A" and relative to the side port 12. The annular shoulder 31 may be used to locate the edge 29 of the cylindrical resilient member 19 within main channel 13. The axial position of the resilient member 19 relative to the side port is important. Whether the cylindrical resilient member 19 is fully seated against the annular shoulder 31 such that the edge 29 is in abutment therewith as shown in FIGS. 1 through 4 or spaced slightly proximal thereto is not as important as the closure of the intersection 18. In particular, the substantially cylindrical resilient member 19 should close the intersection 18 of the side port 12 to the main channel 12 except under flow conditions as illustrated and described in connection with FIG. 3.

The combination valve 10 is preferably molded as one integral piece of resilient material such as an elastomer. The combination valve 10 can be made by assembling a cut piece of tubing and a check valve using adhesives or a welding process such as radio frequency energy or vulcanization. Although the check valve 21 is shown located in the middle of the substantially cylindrical resilient member 19, the check valve 21 can be shifted axially within the check combination valve 10 as required for ease of manufacturing or for enhancing flexibility in use. That is to say that the check valve 21 could be located away from the edge 29 in order to allow flow from the side port 12 to the main channel 13 through the intersection 18 under less pressure. Conversely, the check valve 21 could be located near the edge 29 to reinforce the substantially cylindrical resilient member 19 and thus inhibit flow from the side port 12 through the intersection 18 into the main channel 13. Also various resilient materials could be used to give the required level of flexibility of the substantially cylindrical resilient member 19.

The preferred shape for the substantially cylindrical resilient member 19 is of circular cross section which fits snugly within the main channel 13 which also has a circular cross section of a diameter about the same as the outer diameter of the substantially cylindrical resilient member 19.

The substantially cylindrical resilient member 19 may have an outside diameter dimensioned to provide a snug fit at the proximal end. The distal end of the substantially cylindrical resilient member 19 can be slightly less snug so that the side port valve opening is in the distal direction only. Similarly the main channel 13 can include a slight taper so that the diameter thereof is less about the proximal end of the substantially cylindrical resilient member 19 that the distal end thereof. The preferred taper results from a 0.005 inch decrease in inside diameter from distal to proximal over an axial length of about 0.300 inches.

The check valve 21 includes a web 32 located across the passage 20. There is a slit 33 through the web 32, the slit 33 is cut so that the web 32 provides a normally closed barrier to unpressurized flow, leakage or seepage through the passage, see FIGS. 2 and 3. The web 32 is specifically shaped to open when subject to flow in the direction of arrows labeled "B" in FIG. 4 and to resist opening when subject to flow in a direction opposite thereto. It is preferred that the web shape be sloped like a duckbill so that the slit opens when subject to flow as shown in FIG. 4.

A method for providing the combination valve 10 for the adapter 11 to prevent back flow through the main channel 13 therein and through the side port 12 thereof includes the step of providing the adapter 11 with the main channel 13 and an intersecting side port 12. An additional step places the cylindrical resilient member 19 with the passage 20 therethrough in the main channel 13 to cover the intersection 18 and prevent flow from the outlet 16 of the main channel 13 into the side port 12. An additional step provides the duckbill check valve 21 in the passage 20 to permit flow in the direction shown with arrows "B" in FIG. 4 and to prevent flow in the opposite direction. The method may have an additional step of packaging combination valve 21 and its side port adapter 11 to prevent contamination. The method may also have an additional step of sterilizing the packaged combination valve 10 and its side port adapter 11.

The side port adapter and combination valve hereof is useful to prevent transmission of infection and functions as automatic stop cock valve as well as a multiport adapter for addition to a placed catheter.

What is claimed is:

1. A combination valve for a side port adapter for a catheter to prevent back flow through the side port and through a main channel comprising:
    an adapter having an axis with an inlet and an outlet associated with a main channel along the axis thereof, the adaptor including a side port having an intersection with the main channel to provide access for flow therethrough; and
    a substantially cylindrical resilient member, serving as a one-piece, integrally formed bifunctional valve, having a passage therethrough and having disposed therein substantially normal to the axis and across the passage a check valve which opens when subject to flow in a direction along the axis from the inlet to the outlet and substantially closed to flow in an opposite direction, the substantially cylindrical resilient member closing the side port intersection with the main channel be the resiliency of the member which maintains its cylindrical shape until the intersection open under fluid pressure from the side port exceeding the resiliency which keeps the member cylindrical.

2. The combination valve of claim 1 wherein the adapter has a catheter or other fluid line connected in fluid tight communication with the outlet.

3. The combination valve of claim 1 wherein the adapter has a fluid supply arranged to connect to the inlet and provide flow through the main channel to the outlet.

4. The combination valve of claim 1 wherein the substantially cylindrical resilient member has an edge at a distal end thereof.

5. The combination valve of claim 4 wherein the adapter has an annular shoulder disposed within the main channel distal along the axis and relative to the side port to locate the edge of the cylindrical member within the main channel.

6. A combination valve for a side port adapter to prevent back-flow through the side port and through a main channel comprising:
    an adapter having a main channel along an axis thereof, the adapter including a side port having an intersection with the main channel to provide access for flow therethrough; and
    a cylindrical resilient member serving as a one-piece integrally formed bifunctional valve with a passage therethrough and having disposed therein substantially normal to the axis and across the passage, a check valve which opens with flow along the axis in a direction and closes to flow in an opposite direction, the resilient member normally against the intersection to hold the intersection closed until the member deflects and opens under fluid pressure from the side port that exceeds the resiliency of the member.

7. A combination valve for a side port adapter to prevent back-flow through the side port and through a main channel comprising:
    an adapter having a cylindrically shaped main channel along an axis thereof, the adapter including a side port having an intersection with the main channel to provide access for flow therethrough; and
    a resilient member having a cylindrical shape sized to fit the main channel, serving as a one-piece integrally formed bifunctional valve with a passage therethrough and having disposed therein, substantially normal to the axis across the passage, a check valve which opens with flow along the axis in a first direction and closes to flow in a second, opposite direction, the resilient member normally against the intersection to hold the intersection closed until the member deflects and opens under fluid pressure from the side port that exceeds the resiliency of the member.

8. The combination valve of claim 7 wherein the cylindrical shape has a circular cross section.

9. The combination valve of claim 8 wherein the main channel about the cylindrical resilient member is tapered to hold the cylindrical resilient member more tightly near the inlet than the outlet.

10. The combination valve of claim 7 wherein the check valve includes a web across the passage and a slit in the web and the slit is normally closed.

11. The combination valve of claim 10 wherein the web is shaped to open when subject flow in the one direction and to resist opening when subject flow in the opposite direction.

12. The combination valve of claim 10 wherein the main channel has an axis with an inlet and an outlet associated therewith.

13. The combination valve of claim 12 wherein the outlet is in fluid tight communication with a catheter or other fluid connection.

14. The combination valve of claim 13 wherein the inlet is in fluid communication with a fluid supply arranged to provide flow through the main channel to the outlet.

15. The combination valve of claim 14 wherein the web has a shape of a duck bill that opens when subject flow in the one direction through the duck bill and to resist opening when subject flow in the opposite direction into the duck bill.

16. A method of providing a combination valve in a side port adapter to prevent back flow through a main channel therein and through a side port thereof including the following steps:
providing an adapter with a main channel and a side port with an intersection with the main channel;
placing a cylindrical resilient member, serving as a one-piece integrally formed bifunctional valve, having a passage therethrough in the main channel to cover the intersection and prevent flow from an outlet of the main channel to the side port, and
providing a duck bill check valve in the passage to permit flow through the main channel in a direction and prevent flow in the opposite direction.

17. The method of claim 16 wherein the additional step of packaging the combination valve in a side port adapter to prevent contamination is performed.

18. The method of claim 17 wherein the additional step of sterilizing the packaged combination valve in a side port adapter is performed.

* * * * *